US00PP12195P2

(12) United States Plant Patent
Heims

(10) Patent No.: US PP12,195 P2
(45) Date of Patent: Nov. 6, 2001

(54) HEUCHERA PLANT NAMED 'STRAWBERRY CANDY'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/452,050

(22) Filed: Nov. 30, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Klarquist Sparkman, LLP

(57) ABSTRACT

A new and distinct hybrid of Heuchera plant characterized by large pink flowers, dwarf form, and silver-mottled leaves.

1 Drawing Sheet

The present invention relates to a new and distinct hybrid of Heuchera, of the family Saxifragaceae, which originated as a cross between an unpatented, unnamed *Heuchera sanguinea* seedling (seed parent) and an unpatented *Heuchera cylindrica* named 'Greenfinch' (pollen parent).

This new Heuchera plant is a result of a controlled cross of the aforementioned plants in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Large pink flowers.
2. Dwarf form.
3. Green foliage mottled with silver.

Asexual propagation by division and tissue culture as done in Canby, Oreg., shows that the foregoing characteristics and distinctions come true to form and are established and transmitted through succeeding propagations.

BRIEF DESCRIPTION OF THE DRAWING

The drawing shows Heuchera 'Strawbery Candy' in June in Canby, Oreg.

DETAILED PLANT DESCRIPTION

The following is a detailed description of the new Heuchera hybrid based on observations of one year old specimens grown in the field in Canby, Oreg. The color descriptions are all based on *The Royal Horticultural Society Colour Chart.*

Botanical classification: *Heuchera sanguinea*×*Heuchera cylindrica.*

Foliage:
- *Type.*—Simple. Evergreen.
- *Shape.*—Cordate.
- *Length.*—6 cm.
- *Width.*—5–6 cm.
- *Petiole length.*—8 cm.
- *Margins.*—Dentate-serrate. Ciliolate.
- *Apex.*—Rounded.
- *Base.*—Cordate.
- *Leaf texture.*—Glabrate.

- *Petiole texture.*—Glabrate.
- *Leaf arrangement.*—Rosette.
- *Venation.*—Reticulate.

Size:
- *Height.*—11 cm (1 year old plant grown in Canby, Oreg.).
- *Width.*—31 cm (1 year old plant grown in Canby, Oreg.).

Flower:
- *Type.*—Perfect. Complete. Petals insignificant. Sepals petaloid.
- *Overall/calyx shape.*—Campanulate.
- *Overall/calyx size.*—To 1 cm. deep and 1 cm. wide.
- *Petal count.*—5.
- *Petal size.*—Insignificant, attached to calyx, about 1 mm long and 0.75 mm wide.
- *Petal shape.*—Ovate with a clawed base.
- *Petal texture.*—Satiny.
- *Sepal number.*—5.
- *Sepal shape.*—Fused from receptacle to half way to sepal tip resulting in 5 lobes with acute to rounded sepal apex.
- *Sepal size.*—To 1 cm. long and 3 mm wide (where not fused and at widest point).
- *Sepal texture.*—Pubescent.
- *Ovary position.*—Partly inferior.
- *Carpel number.*—2.
- *Stamen number.*—5.
- *Inflorescence type.*—Panicle.
- *Flower number per inflorescence.*—40–50.
- *Peduncle width.*—3 mm tapering to 1 mm.
- *Peduncle texture.*—Bristly.
- *Blooming height.*—29 cm.
- *Bloom period.*—June to July, sporadic rebloom till early fall.
- *Fragrance.*—None.

Fruit:
- *Type.*—Dehiscent capsules.
- *Fertility.*—Low fertility.
- *Fruit size.*—3 mm long and wide.
- *Seed size.*—Minute (dust-like).
- *Seed shape.*—Elliptic to obovate.

Habit: Clumping.

Disease: Plants grown in Canby, Oreg., display zero susceptibility to disease.

Hardiness: Cold hardy to USDA Zone 4.

Color Characteristics

Foliage:

*Upper surface.*—RHS 191C Greyed-Green Group.

*Upper surface, along veins.*—RHS 137A Green Group.

*Lower surface.*—RHS 148B Yellow-Green Group.

Flower:

*Bud.*—RHS 58B Red Purple Group.

*Petal.*—RHS 55D Red-Purple Group.

*Calyx.*—RHS Red Purple 58B at tip half to Red 56A at base half.

*Anther.*—RHS. 28B Orange Group.

*Ovary.*—RHS 158C Yellow-White Group.

Peduncle: RHS 183A Greyed-Purple Group.

DESCRIPTION OF PARENT PLANTS

The instant plant resulted from a cross between a *Heuchera sanguinea* seedling and *Heuchera cylindica* 'Greenfinch'. The *Heuchera Sanguinen* seedling was selected as a parent plant for its dwarf habit and cerise-colored flowers. The instant plant differs from the *Heuchera sanguinea* seedling in having substantially larger flowers and leaves mottled with silver. *Heuchera cylindrica* 'Greenfinch' was selected for its large flowers and silver-mottled leaves. The instant plant differs from *Heuchera cylindrica* 'Greenfinch' in having larger flowers, red versus tawny-green flowers, and leaves that display a greater degree of mottling.

I claim:

1. A new and distinct hybrid of Heuchera plant substantially as shown and described, characterized by large pink flowers, dwarf form, and silver-mottled leaves.

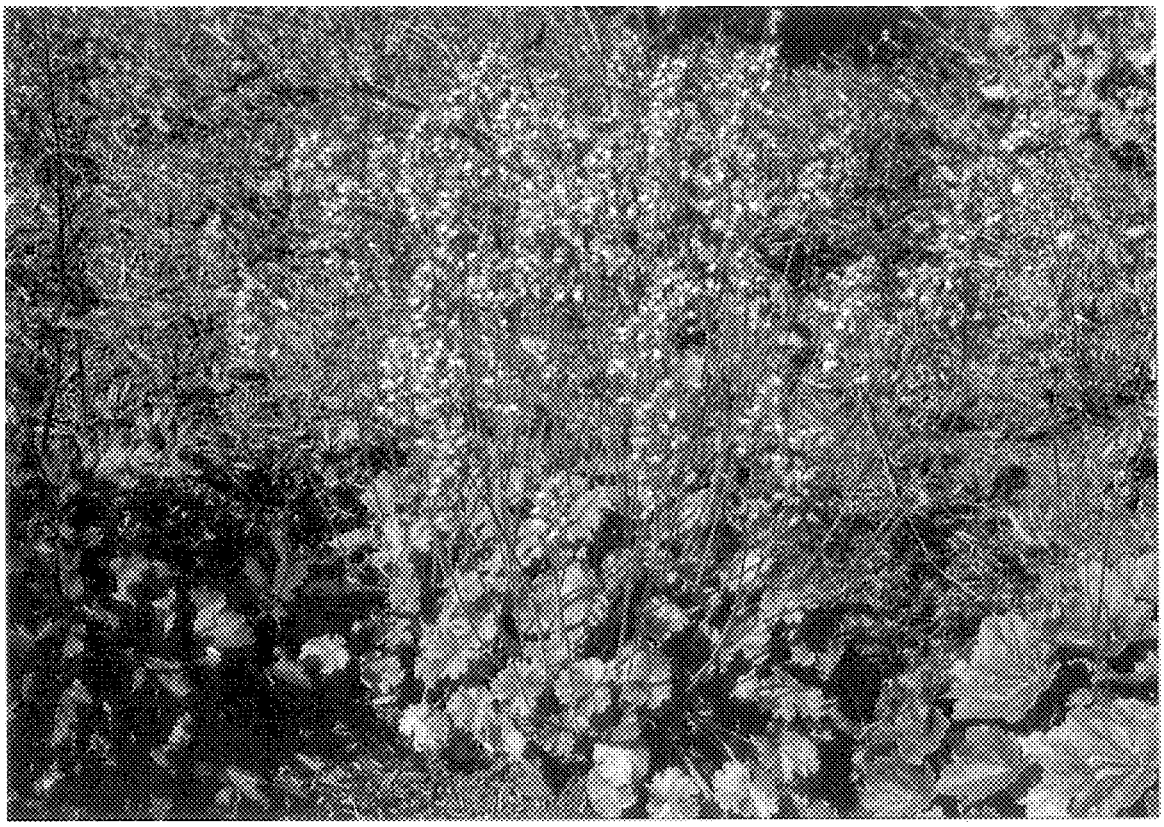

* * * * *